(12) United States Patent
Bair et al.

(10) Patent No.: US 6,586,258 B1
(45) Date of Patent: Jul. 1, 2003

(54) METHOD AND APPARATUS FOR CONFINING A LIQUID SAMPLE FOR THERMAL ANALYSIS

(75) Inventors: Harvey Edward Bair, Chester, NJ (US); Arturo Hale, New York, NY (US); Stephen Reid Popielarski, Narberth, PA (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/568,264

(22) Filed: May 10, 2000

Related U.S. Application Data

(63) Continuation-in-part of application No. 09/291,492, filed on Apr. 14, 1999, now abandoned.

(51) Int. Cl.[7] .............................. B01L 3/00; G01K 17/00
(52) U.S. Cl. .................... 436/174; 359/398; 374/12; 374/31; 374/208; 422/102; 435/305.4; 436/147; 436/164; 436/183
(58) Field of Search .................. 435/305.4; 436/147, 436/164, 174, 183; 422/102; 374/12, 14, 31, 208; 359/398

(56) References Cited

U.S. PATENT DOCUMENTS

| | | | |
|---|---|---|---|
| 2,533,088 A | * | 12/1950 | Brewer et al. |
| 3,589,173 A | | 6/1971 | Hemstock |
| 3,718,561 A | | 2/1973 | Jacob |
| 3,847,819 A | | 11/1974 | Firth |
| 4,064,740 A | | 12/1977 | Crosby, Jr. |
| 4,299,921 A | * | 11/1981 | Youssef |
| 4,815,316 A | | 3/1989 | Tantram |
| 4,974,952 A | * | 12/1990 | Focht |
| 5,525,304 A | * | 6/1996 | Matsson et al. |
| 5,604,130 A | * | 2/1997 | Warner et al. |
| 5,609,826 A | * | 3/1997 | Cargill et al. |
| 5,665,599 A | * | 9/1997 | Minuth |
| 5,837,888 A | | 11/1998 | Mayer et al. |
| 6,048,723 A | * | 4/2000 | Banes |

* cited by examiner

*Primary Examiner*—Jan Ludlow

(57) ABSTRACT

In accordance with the invention, a liquid sample for thermal analysis is disposed within a receptacle having a bottom surface and side walls. The top edges of the side walls are bent towards the center of the receptacle. A sheet of flexible, transparent material substantially impermeable to the sample is disposed across the top edges of the side walls, and an open lid compresses an o-ring onto the sheet material, sealing it against the bent top edges of the receptacle. The bottom surface of the receptacle is advantageously coated with a a material not wetted by the sample such as a fluorcarbon.

12 Claims, 1 Drawing Sheet

METHOD AND APPARATUS FOR CONFINING A LIQUID SAMPLE FOR THERMAL ANALYSIS

CROSS REFERENCE TO RELATED APPLICATIONS

This application is a continuation-in-part of U.S. patent application Ser. No. 09/291,492, filed by H. E. Bair et al. on Apr. 14, 1999 and entitled "Method of Measuring the Permeability of a Material Using Thermogravimetric Analysis Techniques," now abandoned which is incorporated herein by reference.

FIELD OF THE INVENTION

This invention relates to methods and apparatus for confining a liquid sample for thermal analysis. It is particularly useful for confining of volatile liquids in photocalorimetric analysis.

BACKGROUND OF THE INVENTION

Thermal analysis techniques such are highly useful in studying chemical reactions within a liquid. Photocalorimetric analysis, for example, measures the thermal response of a sample upon irradiation with light. Photocalorimetric analysis is widely used in the study of photo-induced polymerization.

Ideally the liquid sample under study should be confined in such a fashion that it cannot escape by evaporation. For photocalormetric analysis, the sample should also be optically accessible in a thin, uniform layer. Evaporation loss and thickness variation would introduce error.

The only commercially available sample containers that can handle volatile samples for thermal analysis have metal covers or lids. They are therefore unsuitable for photocalorimetry because light cannot penetrate through the metal cover. Commercially available sample containers intended for photocalorimetry cannot contain volatile liquids. They consist of an aluminum pan and a quartz window that sits on the pan. The quartz window allows light to penetrate and irradiate the sample; however it does not provide a good seal, so volatile samples can partly or totally evaporate during the measurement. Evaporation is undesirable because the change in mass and the heat of vaporization are sources of error.

A second difficulty with commercially available sample containers is that they often present liquids (or solidified liquids) in films of nonuniform thickness. In order to obtain good results, the thickness of the sample should be uniform. But liquids typically wet the surface of the sample container and form a meniscus. The thickness in the center of the container is smaller than thickness at the walls. Accordingly there is a need for improved methods and apparatus for confining liquid samples in thermal analyses.

SUMMARY OF THE INVENTION

In accordance with the invention, a liquid sample for thermal analysis is disposed within a receptacle having a bottom surface and side walls. The top edges of the side walls are bent towards the center of the receptacle. A sheet of flexible, transparent material substantially impermeable to the sample is disposed across the top edges of the side walls, and an open lid compresses an o-ring onto the sheet material, sealing it against the bent top edges of the receptacle. The bottom surface of the receptacle is advantageously coated with a a material not wetted by the sample such as a fluorocarbon.

BRIEF DESCRIPTION OF THE DRAWINGS

The advantages, nature and various additional features of the invention will appear more fully upon consideration of the illustrative embodiments now to be described in detail in connection with the accompanying drawings. In the drawings.

It is to be understood that these drawings are for purposes of illustrating the concepts of the invention and are not to scale.

DETAILED DESCRIPTION

Figure 1:
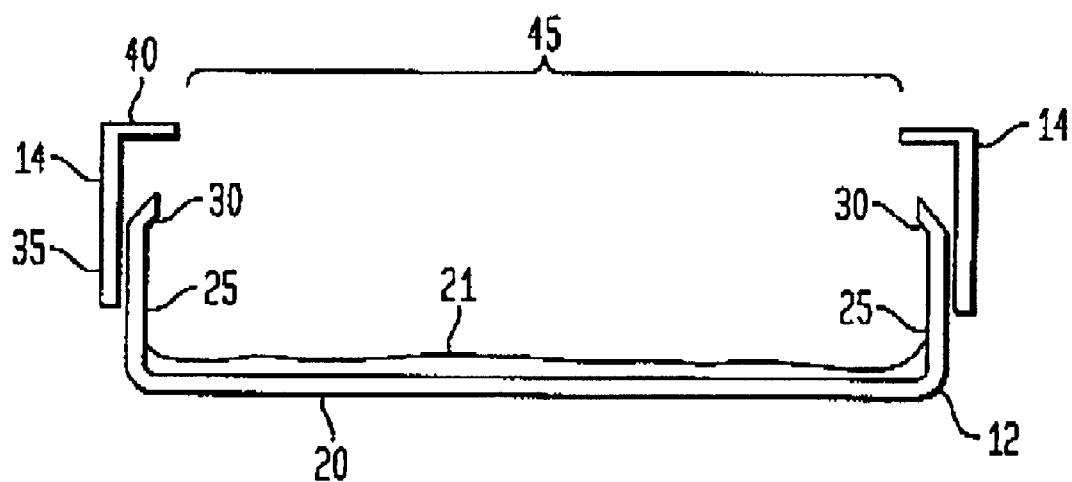
FIG. 1 is a cross-sectional view of a receptacle and a receptacle lid useful for containing a liquid sample in thermal analysis.

Referring to the drawings, FIG. 1 illustrates a receptacle 12 and a receptacle lid 14 of a liquid sample container. The receptacle 12 has a bottom surface 20 and side walls 25. The top edges 30 of the side walls are bent towards the center of the receptacle. The bend angle is typically less than 45°, and the length of the bent edge can be about 0.75 mm. The receptacle lid 14 has a top surface 40 and side walls 35. The receptacle 12 and the receptacle lid 14 are configured so that the side walls 25, 35 form a seal when the receptacle lid 14 is placed upon the receptacle 12.

The top surface 40 of the receptacle lid 14 has a hole 45 therein. The hole 45 has an area that is less than 95% of the top surface of the lid 14 and preferably less than about 80% of the area of the lid. Holes 45 with areas greater than about 80% of the area of the receptacle lid 14 potentially interfere with the formation of the seal between the receptacle 12 and the receptacle lid 14.

The receptacle 12 and the receptacle lid 14 are each made of a material which is impermeable to the sample placed therein. Examples of suitable materials include metals such as aluminum and stainless steel, or glass. Receptacles and receptacle lids (without holes) are available from Perkin-Elmer Company, Norwalk, Conn.

Advantageously, the bottom surface 20 of the receptacle 12 is coated with a material 21, such as a fluorocarbon polymer, to prevent the liquid sample from wetting the surface 20. This prevents formation of a meniscus and presents a uniform thickness of the sample. The coating 21 can extend up the side walls 25 of the receptacle.

Figure 2:
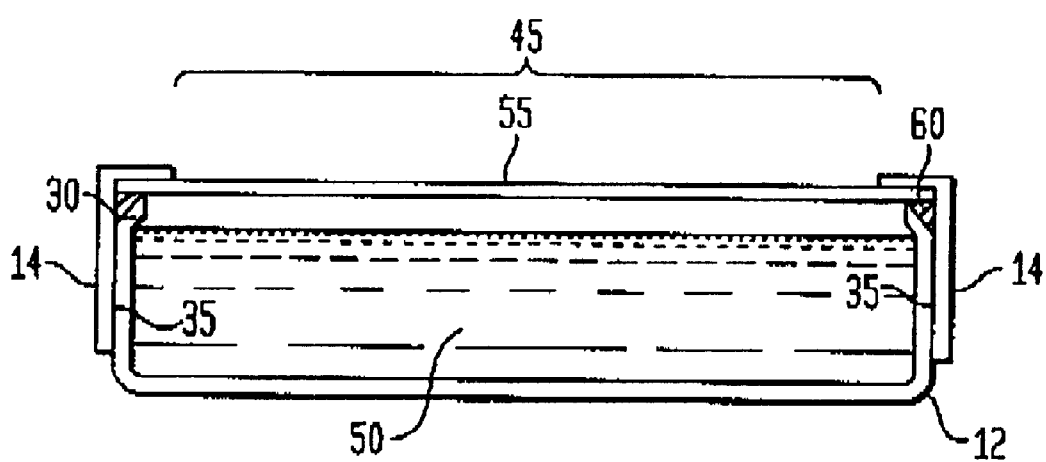
FIG. 2 is a cross-sectional view of the container of FIG. 1 provided with an impermeable sheet material and a deformable ring for confining the liquid sample.

A sealed receptacle is assembled by filling the receptacle 12 with a sample liquid 50 (or solid or gas), as show in FIG. 2. Thereafter, an impermeable material sheet 55 is placed in the receptacle lid 14 so that it covers the bole 45 therein. The receptacle lid 14 is then compressed onto the receptacle 12 to form the sealed receptacle 12. The sheet 55 and hole 45 can provide a window for optical access to the enclosed sample.

The sheet material 55 should be transparent to the light to be used in analyzing the sample (typically light of wavelength in the range 200–900 nm). The sheet should have a leak rate of less than about 1.5 weight %/hr. for the sample to be tested. Advantageously the sheet material is a transparent polymer such as polyvinylidene chloride. Another advantageous sheet material is a copolymer of polyhexafluoropropylene and polytetrafluoroethylene. The sheet material is typically at least one micrometer thick.

The receptacle is optionally sealed with a deformable material 60. The deformable material 60 is placed in the receptacle lid 14 on the material sheet 55 along the perimeter of the side-walls 35 of the lid, before the receptacle lid 14 is compressed on the receptacle 12. The deformable material preferably is in the form of an o-ring. A typical diameter is about 0.6 mm. Examples of suitable deformable materials include rubber, silicone rubber, thermoplastic elastomers, thermosets, and hydrophobic materials such as hydrocarbon waxes and Teflon.

When the receptacle 12 is sealed with the deformable material 60, it is desirable for the top edges 30 of the receptacle side-walls 25 to be bent towards the center of the receptacle 12. Bending the top edges 30 of the receptacle side-walls 25 toward the center of the receptacle 12 facilitates the formation of the seal between the receptacle 12, the deformable material 60, and the material sheet 55 when the receptacle lid 14 is placed thereon.

The top edges 30 of the receptacle side-walls 25 are preferably bent towards the center of the receptacle 12 at an angle of less than about 60 degrees and typically less than 45. The bent edges 30 preferably have a length less than about 0.8 mm.

It is to be understood that the above-described embodiments are illustrative of only a few of the many possible specific embodiments which can represent applications of the principles of the invention. Numerous and varied other arrangements can be readily devised by those skilled in the art without departing from the spirit and scope of the invention.

What is claimed:

1. A method of confining a liquid sample within a container for thermal analysis, comprising the steps of:

providing a receptacle, a lid wherein the lid has a top surface, a bottom surface opposite the top surface, and a sidewall, the bottom surface and sidewall defining an interior, a deformable sealant, and at least one sheet of material transparent to light of wavelength of from about 200 nanometers to about 900 nanometers, wherein the at least one sheet of material has a leak rate for the sample of less than about 1.5 wt. %/hr.;

placing the sample of a liquid in the receptacle;

placing the sheet of material in the lid, wherein the sheet of material is in contact with the bottom surface of the lid;

placing the deformable sealant in the lid along the perimeter of the sheet of material; and compressing the lid onto the receptacle forming a container with the sample of the liquid sealed therein.

2. The method of claim 1 wherein the lid is made of metal.

3. The method of claim 2 wherein the metal is selected from the group consisting of aluminum and steel.

4. The method of claim 1 wherein the deformable sealant is an o-ring.

5. The method of claim 1 wherein the deformable sealant is a material selected from the group consisting of rubber, silicon rubber, thermoplastic elastomers, and epoxy.

6. The method of claim 1 wherein the sheet of material is at least 1 micron thick.

7. The method of claim 1 wherein the at least one sheet of material is selected from the group consisting of a polymer, and a glass.

8. The method of claim 7 wherein the polymer is selected from the group consisting of poly(vinylidene chloride) and poly(hexafluoropropylene-co-tetrafluoroethylene).

9. The method of claim 1 wherein the bottom of receptacle is coated with a material which is not wetted by the liquid sample.

10. The method of claim 1 wherein the liquid is confined within the container in an inert atmosphere.

11. The method of claim 1 wherein the top surface of the lid has a window therein.

12. The method of claim 11 wherein the window covers less than about 95% of the top surface of the lid.

* * * * *